United States Patent [19]
Damgaard et al.

[11] Patent Number: 6,030,828
[45] Date of Patent: Feb. 29, 2000

[54] MICROSENSOR AND USE OF SUCH MICROSENSOR

[75] Inventors: Lars Riis Damgaard, Aarhus C, Denmark; Niels Peter Revsbech, Aarhus N, Denmark

[73] Assignee: Unisense APS., Aarhus C, Denmark

[21] Appl. No.: 09/068,202

[22] PCT Filed: Nov. 22, 1996

[86] PCT No.: PCT/DK96/00488

§ 371 Date: May 1, 1998

§ 102(e) Date: May 1, 1998

[87] PCT Pub. No.: WO97/19345

PCT Pub. Date: May 29, 1997

[30] Foreign Application Priority Data

Nov. 22, 1995 [DK] Denmark .................................. 1313/95

[51] Int. Cl.[7] .................................................. C12M 3/00
[52] U.S. Cl. ........................... 435/287.1; 435/287.5; 435/288.7; 435/808; 435/817; 204/403; 204/415; 356/317; 356/345; 356/432
[58] Field of Search ................................. 204/403, 415; 205/777.5, 778, 783; 435/287.1, 287.5, 288.7, 808, 817; 356/317, 345, 432

[56] References Cited

U.S. PATENT DOCUMENTS

| | | | |
|---|---|---|---|
| 3,709,812 | 1/1973 | Niedrach | 204/195 P |
| 3,900,382 | 8/1975 | Brown, Jr. | 204/195 |
| 3,957,613 | 5/1976 | Macur | 204/195 M |
| 4,627,907 | 12/1986 | Niedrach et al. | 204/415 |
| 4,780,192 | 10/1988 | Christiansen et al. | 204/415 |
| 5,476,001 | 12/1995 | Hoetzel et al. | 73/23.31 |

*Primary Examiner*—David A. Redding
*Attorney, Agent, or Firm*—Lee, Mann, Smith, McWilliams, Sweeney & Ohlson

[57] ABSTRACT

The invention relates to a microsensor for determining the concentration of a primary substrate by measuring the concentration of a secondary substrate. The microsensor comprises a transducer (1) for measuring the secondary substrate. The transducer (1) is surrounded by a first casing (8), which has an opening (9) with a barrier (10). The first casing (8) surrounds a second casing (11), also with an opening (12) with a barrier (13). In the first casing (8) between the barrier (10) and barrier (13), a reaction space (15) is formed. In the reaction space (15) an environment with catalytic components is contained. By measuring the concentration of the secondary substrate, the presence of the primary substrate can be determined.

27 Claims, 6 Drawing Sheets

MICROSENSOR AND USE OF SUCH MICROSENSOR

INTRODUCTION TO THE DESCRIPTION

The present invention relates to a microsensor for measuring the concentration of a primary substrate in the surrounding environment which can be a fluid, a gas or a matrix, which microsensor comprises a first casing with an opening, which opening is in contact with a first barrier and a reaction space which borders on the first barrier, in which reaction space a catalytic material is located, a material intended to catalyse a conversion of the primary substrate with the concomitant conversion of a secondary substrate, and which microsensor furthermore comprises a transducer for the secondary substrate, which transducer is located at a distance from the first barrier.

Different types of biosensors for measuring the concentration and partial pressures of different primary substrates are known. J. Chem. Tech. Biotechnol. 44, 85–106 (1989) describes different methods and different sensors. However, the sensors described have various disadvantages. For measuring the concentration of the primary substrate, for instance methane, in an environment, it is necessary that the secondary substrate, for instance oxygen, is present in the environment in which the primary substrate is to be measured. Consequently, if the concentration of the secondary substrate is unknown or zero, it is not possible to measure the concentration of the primary substrate. Furthermore, it has been shown that in sensors depending on several substrates which are initially added to the reaction space, these substrates can be depleted or degraded. Finally, the sensors described are not miniaturised, which leads to extensive diffusive distances and response times, and in-situ measurements is difficult.

European Journal of Applied Microbiology and Biotechnology 10, 235–243 (1980) describes a biosensor, comprising a first vessel containing a microbiological fluid in which measurements are to be made and a second vessel containing an electrolyte and cathodes and an anode submerged in the electrolyte. Between the first and the second vessel two Teflon® membranes are placed, between which agar with immobilised Clostridium butyricum is deposited.

However, this sensor has several disadvantages. Measurements are very sensitive to whether sufficient stirring is established in the fluid, in which the measurements are to be made. Thus it is necessary to provide a constant stirring of the fluid. Furthermore, it is not possible to make in-situ measurements, as samples have to be taken for the measurement. Consequently, precise measurements over time are difficult to make and so are measurements with high spatial resolution. The necessity of stirring and the sensor construction in general makes the sensor unsuited for measurements at the location in question, for instance a bio-gas reactor.

Electroanalysis, 1 (1989) 305–309 describes a sensor type, comprising a silicon core, plated with silicon oxide on an outer and on an inner surface. The silicon core is furnished with gold electrodes and a chamber containing alginate. A gas permeable membrane is covering the gold electrodes and contains a reservoir containing immobilised bacteria. The gas permeable membrane makes a barrier between the chamber containing the alginate and the reservoir with the immobilised bacteria.

Due to the physical design of this sensor and other macroscopic sensors that consume an analyte in the process of measuring with a one-dimensional direction of diffusion, the role of a diffusive boundary layer will be significant, making such sensors very sensitive to the degree of stirring and thus unsuited for in-situ measurements. The sensor described above needs both the primary substrate, which is to be measured, and the secondary substrate to be present in the environment. The nutrition in the alginate in the sensor will further limit the use of the sensor as the bacteria will die, and $CO_2$, which is the primary substrate for this sensor, will be released by the bacteria, affecting the measurement when the bacteria die, as the nutrition in the alginate is depleted by the bacteria.

The purpose of the present invention is to produce a biosensor, which is miniaturised, improving the properties of the sensor and enabling continuous (on-line) measurements without a need to take out samples, which makes measurements with a high spatial resolution possible even in steep chemical gradients, and which is secured a constant supply of the secondary substrate for measuring the primary substrate in an environment. Thus the sensor is well suited for in-situ measurements.

This is achieved with a sensor, which is characterised by that the microsensor comprises a second casing, that the second casing is furnished with an opening in contact with a second diffusion permeable barrier, that the second barrier is established at a distance from the first barrier so that the reaction space is formed in the first casing between the first barrier and the second barrier, and that the second casing constitutes a source of the secondary substrate.

A sensor with these characteristics produces a sensor which is very precise and which without problems makes it possible in-situ to make very precise measurements and gradient measurements in the environment to be analysed, for instance a fluid, a matrix, or a gas, without the need for using for instance a pipette to take out samples. The second casing enables a constant supply of and measurement of a second substrate. Thus it is possible to make constant measurements of the primary substrate as mentioned above. The measurement of the second substrate is made in a position between the opening of the first casing and a face of the barrier of the second casing, which faces the interior of the second casing.

In experiments with the sensor according to the invention using methane as the primary substrate, interference from other compounds such as acetate, sulphide and ammonia was investigated. The experiments showed that these compounds have a negligible effect as only very high concentrations of sulphide was shown to have an effect.

Interference from different pH values in the fluid wherein the measurements were made was practically zero and deviated only as a consequence of using different buffers and of the different physical properties of these buffers. Results showed an interference of less than 4% between measurements at pH 7 and pH 10, respectively.

The temperature of the environment in which measurements are made will influence the measurements to some extent. Furthermore, the sensor cannot be used above the temperatures at which the chemical or biological components used in the reaction space will be inactivated.

If the secondary substrate is oxygen, the transducer is preferably a Clark-type oxygen microsensor, but other types, such as fibre-optic oxygen microsensors, may also be used. The barriers, produced in the openings of the first and second casing, are preferably made in silicone rubber. Ion-permeable materials may also be used. Hereby the use of the sensor can be expanded to comprise not only gasses, but also ions and other polar compounds, if the catalytic material in the reaction space is replaced by another catalytic material, for instance a different bacterial culture, capable of metabolising these compounds.

The measurements made with the sensor can be made in-situ and within a response time of below ½ minute. Thus a certain presence for instance of methane in for instance a fluid can be measure within a short time and can be measured continuously over a given period of time. Among other things, the response time depends on the distance between the transducer and the opening of the first casing.

The diffusive distance in the first casing from the opening of the first casing and inwards in the first casing can be limited by producing a so-called back guard, which can be electrochemical or of another type. A back guard is preferably placed in the first casing and consumes that part of the primary and/or secondary substrate, which is not consumed in the reaction space. Thus, the maximal diffusive distance for the substrates from the opening and inwards in the first casing will be the distance from the opening of the first casing to the back guard. A back guard of this type can be electro-chemical, for instance a Clark-type element removing oxygen. Alternatively, the back guard functions by establishing a fixed concentration of the primary or secondary substrate. A back guard of this type can be for instance a gas phase, which inwards in the first casing replaces the aqueous medium, and which, due to its high capacity for assimilating gasses and high diffusivity of gasses, can provide a fixed background concentration of the primary and/or the secondary substrate. In this case the back guard can be a so-called window, surrounding the transducer.

Experiments have shown that the sensitivity to stirring is less than 2%. Thus, the sensor according to the invention has no need for stirring. Furthermore, it is possible to produce sensors with a signal, which is linear in the partial pressure range 0–1 atm. methane and sensors with a sensitivity of below 0.001 atm. methane.

Alternatively, or as a supplement to the back guard, the microsensor according to the invention can be furnished with a so-called front guard. The purpose of the front guard is to establish a stable and controlled environment, for instance free of secondary substrate or other interfering compounds, around the opening of the first casing without preventing the diffusion of the primary substrate from the surrounding environment into the first casing. The front guard may be a third casing surrounding the first casing which has an opening with a barrier which is located at a distance from the first barrier, thus creating an additional space around the first casing. By placing for instance a bacterial culture which consumes the secondary substrate, for instance oxygen, but which does not consume the primary substrate, for instance methane, in the third casing, the secondary substrate, for instance oxygen, from the surrounding environment can be eliminated. However, the addition of a third casing will increase the physical dimensions of the sensor, which in turn increases the response time.

The sensor according to the invention is primarily intended for the measurement of ethanol, methanol, ammonium and methane in microbial ecology, medicine, and in the control of industrial processes, including waste water treatment plants. Industries producing measuring equipment and industries producing organic compounds in fermentors are suited areas for the use of the sensor according to the invention. Furthermore, the sensor is well suited for use in bio-gas reactors and laboratories.

DESCRIPTION OF THE DRAWING

In the following the invention will be described referring to the enclosed drawings, where.

Figure 1:
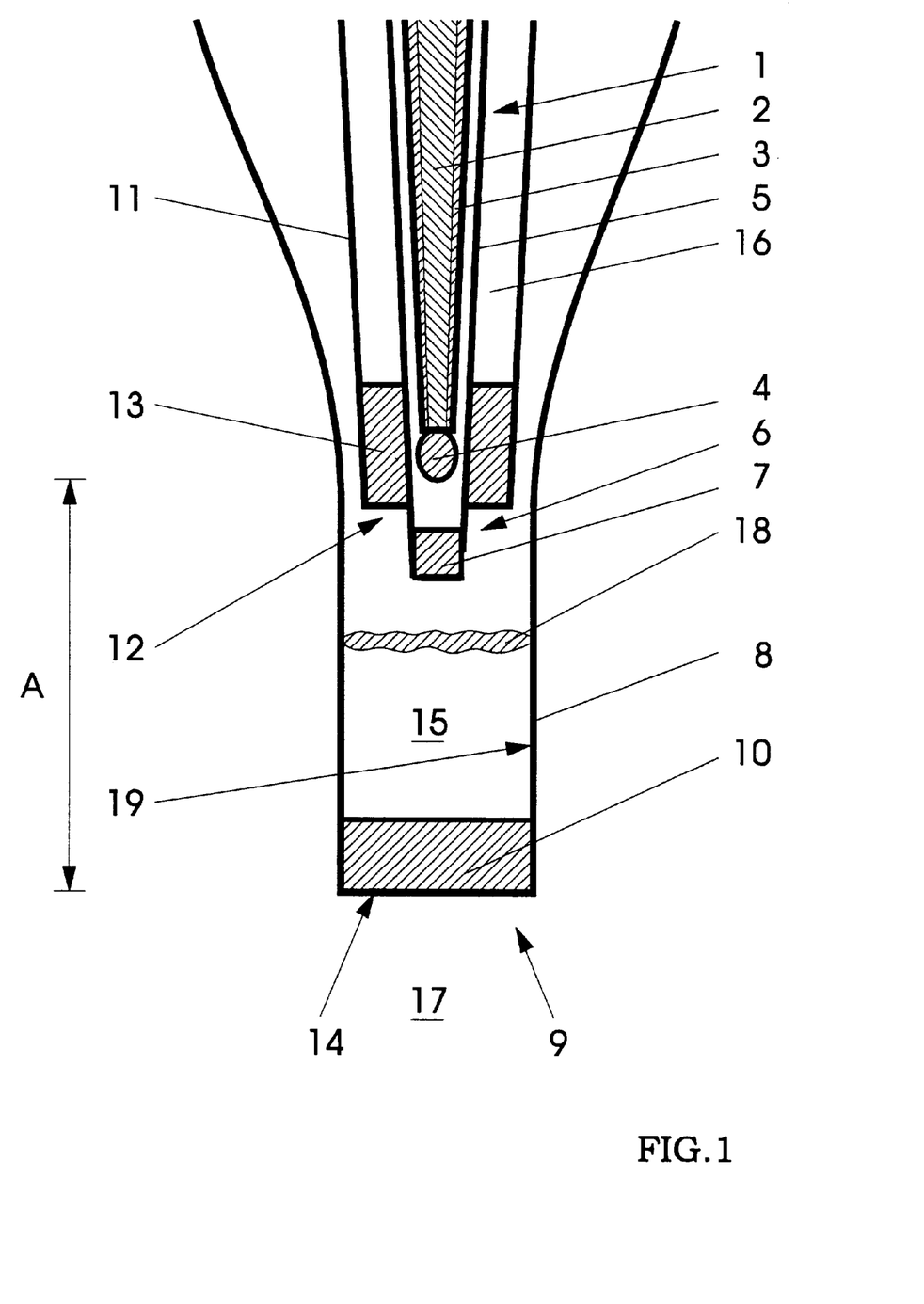
FIG. 1 is a section through a possible schematic embodiment of a microsensor according to the invention.

FIG. 1 illustrates an embodiment of the front part of a microsensor according to the invention. The microsensor comprises a transducer in the form of an oxygen microsensor 1, which in the shown embodiment is a Clark-type oxygen microelectrode. The Clark-type oxygen microelectrode includes a cathode 2. The cathode 2 has an exposed tip 4. The rest of the cathode is coated with a thin layer of electrically insulating material 3, preferably glass. The cathode 2 is enclosed in a tube 5. A tip 6 of the Clark-type oxygen microelectrode is mounted in a diffusion permeable barrier 7. A first casing 8, which in a preferred embodiment is made of glass, has an opening in the form of an orifice 9, which is in sealing contact with and encompassing a first barrier in the form of a first plug 10, which is made of silicone rubber. In the following, the first casing 8 will be referred to as the media casing.

A second casing 11, which is also made of glass in a preferred embodiment, surrounds the Clark-type oxygen microelectrode 1 inside the first casing 8. The second casing 11 has an opening in the form of an orifice 12, which is in sealing contact with and encompassing a second barrier in the form of a second plug 13. The Clark-type oxygen microelectrode 1 is mounted in the second plug 13, which in a preferred embodiment is made of silicone rubber. The tip 6 of the Clark-type oxygen microelectrode 1 is situated at a distance A from a face 14 of the first plug 10 in the orifice 9 of the first casing 8. In the following, the second casing 11 will be referred to as the gas casing.

Between the second plug 13 and the first plug 10, subsidiary the orifice 12 of the gas casing 11 and the orifice 9 of the media casing 8, is provided a reaction space 15. The reaction space 15 is meant to hold a medium in the form of a liquid containing a catalytic material. The catalytic material can be a certain bacterial culture for the oxidation of the primary substrate which is to be measured. In the present embodiment methane is the substance to be measured. However, it is possible to use the microsensor according to the invention to determine the concentration of other primary substrates in the surrounding environment, which environment can be fluids, matrixes and gasses.

A space 16 between the Clark-type oxygen microelectrode 1 and the gas casing 11 contains a certain percentage, preferably an atmospheric percentage, of oxygen $O_2$. The oxygen can diffuse from the space 16 into the reaction space 15 through the second plug 13. The reaction space 15 contains bacteria in a buffered nutrient medium and can be sucked in to the reaction space by applying vacuum at the upper end (not shown) of the microsensor. Methane present in the surrounding environment in a location 17 outside the media casing 8, and which is to be measured, can diffuse into the reaction space 15 through the first plug 10.

Figure 3A:
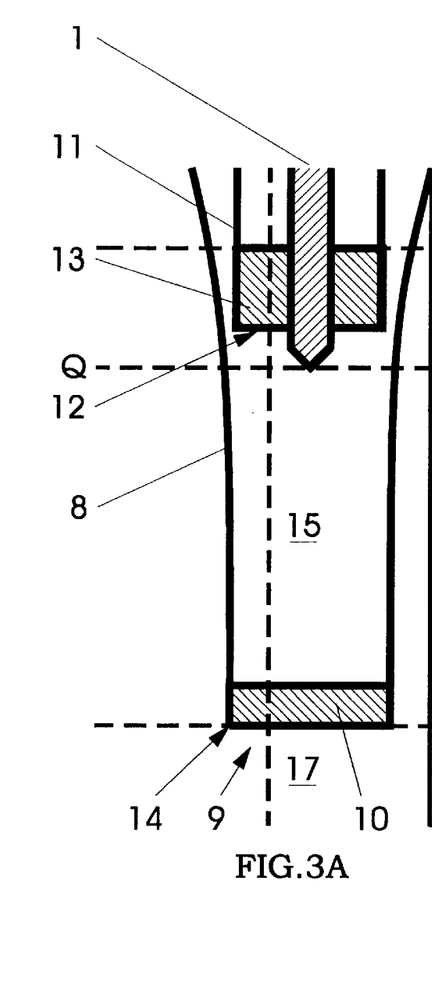
FIG. 3A is a section through a schematic illustration of a microsensor according to the invention

In the reaction space 15 a reaction zone 18 will form (see FIG. 3A). The reaction zone 18 will form in the medium in the reaction space 15 and consists of bacteria cells that have multiplied. The reaction zone 18 extends as a disc with a circumference along an inner surface 19 of the media casing 8, along the media casing 8 and along a circumference of the media casing 8. The reaction zone 18 will form under the influence of equilibrium concentration gradients of oxygen and methane in the reaction space. The equilibrium gradients depend on the diffusional characteristics of the sensor components.

In a preferred embodiment the tip 6 of the oxygen microelectrode 1 has a diameter of 1 $\mu$m to 250 $\mu$m, preferably between 1 $\mu$m and 100 $\mu$m, most preferred between 1 $\mu$m and 10 $\mu$m.

Figure 2:
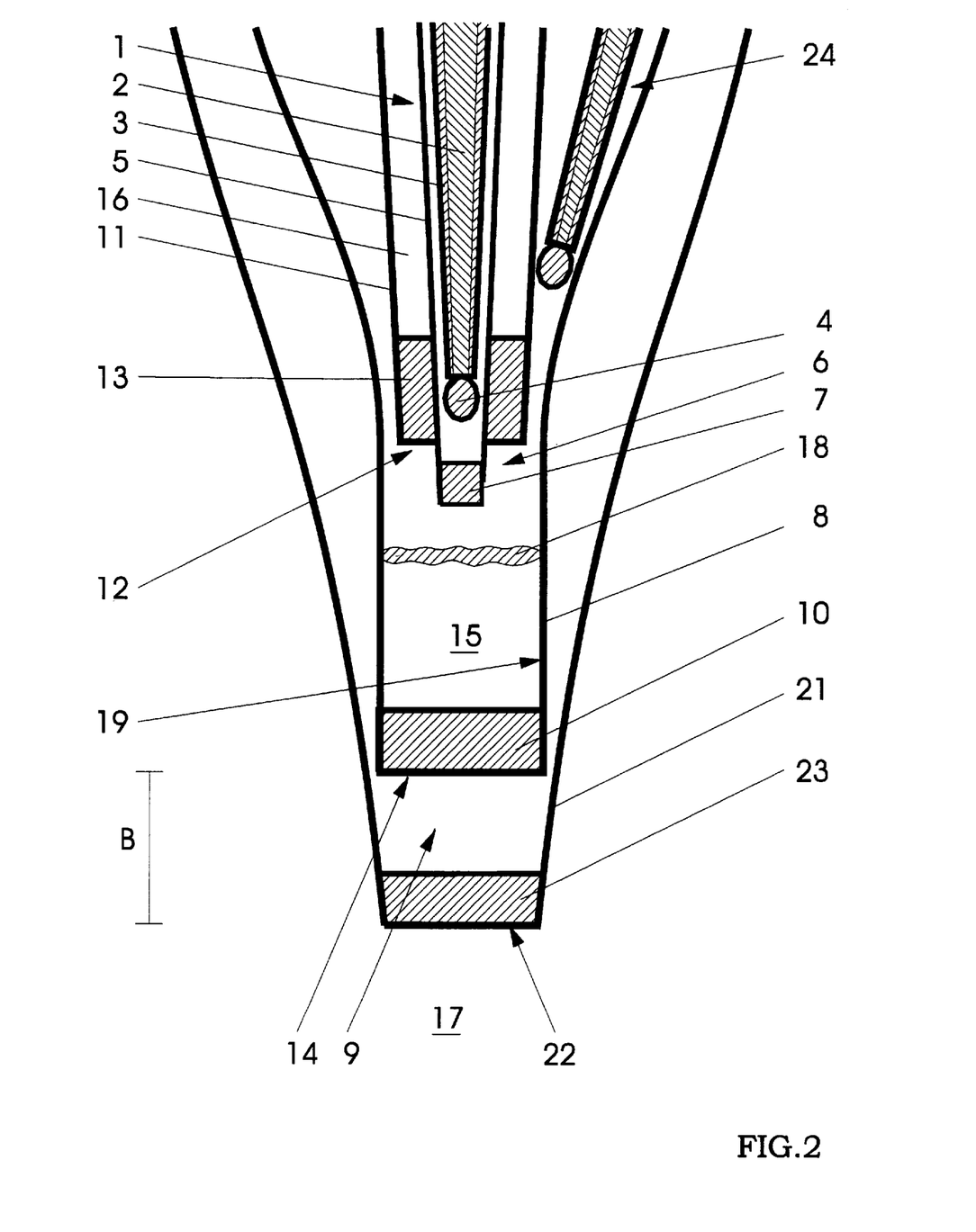
FIG. 2 is a section through an alternative schematic embodiment of a microsensor according to the invention.

FIG. 2 illustrates an alternative embodiment of the microsensor according to the invention. In the alternative embodiment the microsensor according to the invention is furnished with a third casing 21, which surrounds the first casing 8 in a similar fashion as the first casing 8 surrounds the second casing 11. The third casing 21 has an opening in the form of an orifice 22, which is in sealing contact with a third barrier in the form of a third plug 23 in a similar fashion as the orifice 9 of the first casing 8 is in sealing contact with the first plug 10. The third casing contains an electrochemical or biological trap for trapping for instance $O_2$ and sulphide. The third casing constitutes a front guard. The microsensor is also furnished with a back guard 24 in the form of an electrode, which is placed between the first casing 8 and the second casing 11.

FIG. 3A–3D illustrate measurements of methane concentrations using the sensor according to the invention. In FIG. 3A is shown a crude schematic illustration of the Clark-type oxygen microelectrode 1, the media casing 8, the first plug 10, the gas casing 11, and the second plug 13. The reaction space 15 is located between the first plug 10 and the second plug 13.

Figure 3B:
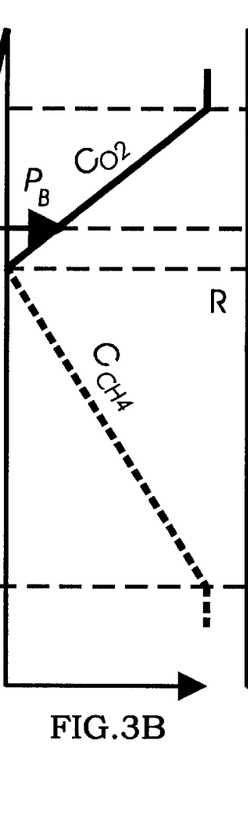
FIG. 3B–3G are schematic illustration of courses of concentrations of a primary substrate and a secondary substrate.
Figure 3C:
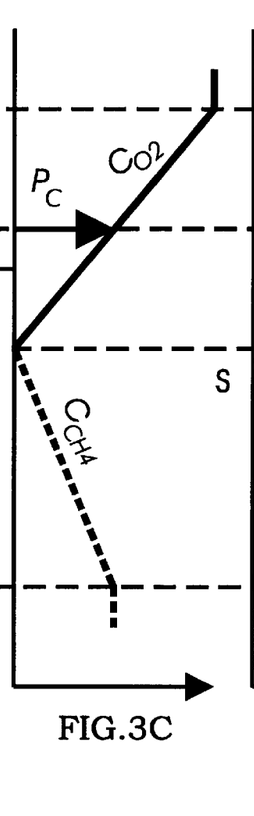
Figure 3D:
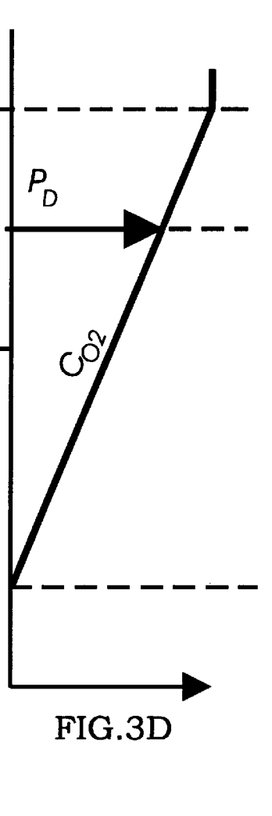

A gradient of the concentration of $C_{CH4}$ of methane and a gradient for the concentration $C_{O2}$ of oxygen is illustrated in FIG. 3B–3D. For the purpose of illustration the concentration gradients are shown to be linear, and the effect of differences in diffusion coefficients in the medium contained in the reaction space 15 and in the plugs 10, 13 is thus not shown.

Other curves for the concentration gradients, linear as well as non-linear, may occur. In the case illustrated here it is assumed that the bacteria in the reaction zone consume all oxygen and all methane in the reaction zone. However, cases where not all oxygen and/or not all methane is consumed may occur. The curves for their concentration gradients will be different in such cases.

The measurement of the secondary substrate takes place at the distance A from the lower face 14 of the first plug 10 in a plane Q, where the tip of the Clark-type oxygen microelectrode 1 is located. The measurement is a measurement of the concentration $C_{O2}$ of oxygen in the plane Q.

FIG. 3B shows a measurement with a relatively high concentration $C_{CH4}$ of methane in the location 17 in the surrounding environment outside the media capillary 8. The concentration is shown as partial pressure in the figure. The concentration of methane decreases from a concentration at the lower face 14 of the first plug 10 through the first plug 10 and through the reaction space 15 being reduced to zero percent in the reaction zone 18. For this concentration of methane at the location 17 in the surrounding environment at the orifice 9 of the first casing 8, the reaction zone is located in a plane R as the ratio between the fluxes of methane and oxygen in this plane is the same as the ratio with which the two substrates participate in the methane oxidation reaction.

A concentration $C_{O2}$ of oxygen is shown as partial pressure in the figure. The concentration of oxygen decreases from a concentration in the gas casing 11 at the upper face 20 of the second plug 13 through the second plug 13 and through the reaction space 15 to zero percent in the reaction zone 18.

FIG. 3C shows a measurement with a relatively low concentration $C_{CH4}$ of methane in the location 17 in the surrounding environment outside the media casing 8. The concentration of methane decreases from a concentration at the lower face 14 of the first plug 10 through the first plug 10 and through the reaction space 15 being reduced to zero percent in the reaction zone 18. At this concentration of methane at the location 17 in the surrounding environment at the orifice 9 of the first casing 8, the reaction zone 18 is located at a plane S.

A concentration $C_{O2}$ of oxygen is shown as partial pressure in the figure. The concentration of oxygen decreases from a concentration in the gas casing 11 at the upper face 20 of the second plug 13 through the second plug 13 and through the reaction space 15 to zero percent in the reaction zone 18. It can be seen that the reaction zone 18, where the ratio of between the fluxes of methane and oxygen correspond to the ratio at which they participate in the reaction, has moved closer to the first plug 10. As a consequence, the concentration of oxygen measured by the Clark-type oxygen microsensor has increased.

FIG. 3D illustrates the same components as in FIG. 3B and 3C, but in FIG. 3D the measurement is done at the location 17 in a surrounding environment which does not contain methane. Consequently, only the concentration of oxygen is illustrated. The concentration $C_{O2}$ of oxygen decreases from a concentration in the gas casing 11 at the upper face 20 of the second plug 13, through the reaction space 15, and further through the first plug 10 to zero percent at the lower face 14 of the first plug 10. In the case illustrated here, the concentration decreases linearly. As there is no methane in the surrounding environment at the location 17 outside the first casing 8, the bacteria in the reaction zone 18 will not be active and not consume any oxygen. It can be seen that the concentration of oxygen measured by the Clark-type oxygen microsensor has increased further compared to in FIG. 3B and 3C.

As mentioned, the measurement of the concentration $C_{O2}$ of oxygen takes place in a plane perpendicular to the longitudinal direction L. In FIG. 3B a measurement corresponding to the arrow $P_B$ will be made, in FIG. 3C a measurement corresponding to the arrow $P_C$ will be made, while in FIG. 3D a measurement corresponding to the arrow $P_D$ will be made. By a calibration of the sensor according to the invention in external media with a known concentration of methane, the signal from the Clark-type oxygen microsensor can be translated into a measure of the concentration $C_{CH4}$ of methane in the surrounding environment. That, among other things, makes it possible to calibrate the microsensor. FIG. 3B and 3C show that the plane R, subsidiary S, in which the reaction zone is located will be dislocated when the concentration of methane $C_{CH4}$ in the surrounding environment at the location 17 is changed.

Figure 3E:
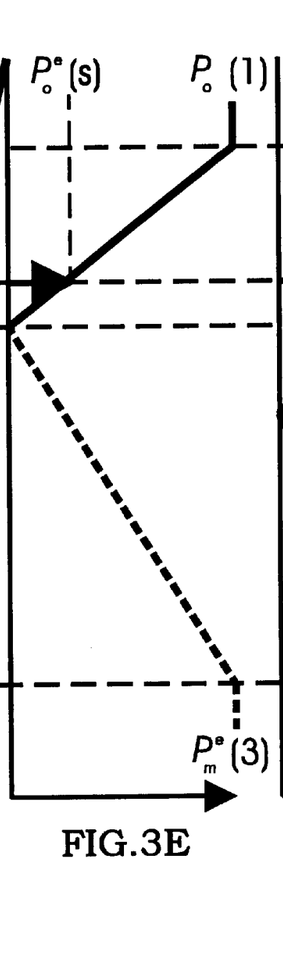
Figure 3F:
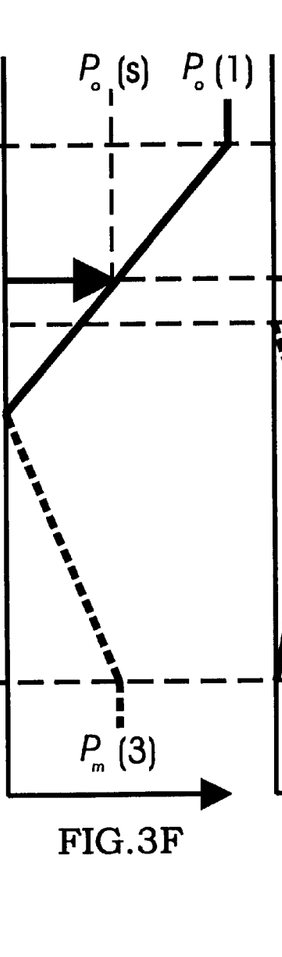
Figure 3G:
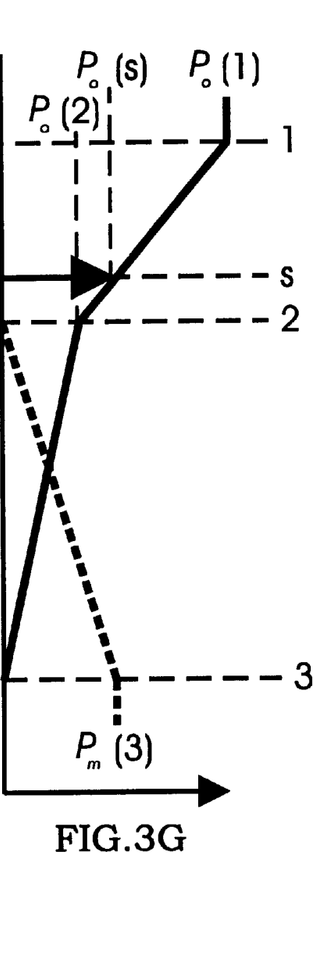

FIG. 3E, FIG. 3F, and FIG. 3G illustrate the gradients of the concentrations of methane $C_{CH4}$ and oxygen $C_{O2}$ in cases, where it is not possible for the reaction zone to move as a response to a change in the concentration of methane $C_{CH_4}$. For the purpose of illustration the concentration gradients decrease linearly and the differences in diffusion coefficients in the medium in the reaction space 15 and in the plugs 10, 13 is thus not accounted for.

FIG. 3E shows a measurement corresponding to a measurement as shown in FIG. 3B with a relatively high concentration $C_{CH_4}$ of methane in the surrounding environment at the location 17 outside the media casing 8 as in FIG. 3C. The concentration is shown as partial pressure in the figure. The relatively high concentration $P_m^e(3)$ of methane is applied for the initial enrichment of the methane consuming bacterial culture. At this relatively high concentration of methane at the location 17 in the surrounding environment at the orifice 9 of the first casing 8, the reaction zone is located in a plane T.

FIG. 3F shows a measurement corresponding to a measurement as shown in FIG. 3C with the same relatively low concentration $C_{CH_4}$ of methane in the surrounding environment at the location 17 outside the media casing 8 as in FIG. 3C. The concentration is shown as partial pressure. The concentration of methane decreases from a concentration $P_m(3)$ at the lower face 14 of the first plug 10 through the first plug 10 and through the reaction space 15, being reduced to zero percent in a plane below the plane T, where the reaction zone is located.

Correspondingly, the concentration of oxygen in the figure is shown as a partial pressure $P_o(S)$. The concentration of oxygen decreases from a concentration $P_o(1)$ in the gas casing 11 at an upper face 20 of the second plug 13 through the second plug 13 and through the reaction space 15 to zero percent in the plane below the plane where the reaction zone is located.

FIG. 3G shows a measurement at the same concentration $C_{CH_4}$ of methane in the surrounding environment at the location 17 outside the media casing 8 as in FIG. 3F. The concentration is shown as partial pressure in the figure. The concentration decreases from a concentration $P_m(3)$ at the lower face 14 of the first plug 10 through the first plug 10 and through the reaction space 15 being reduced to zero percent in the reaction zone 18. For this concentration of methane in the surrounding environment at the location 17 by the orifice 9 of the first casing 8, the reaction zone 18 is located in the plane T, which is the same plane as in FIG. 3E and FIG. 3F.

Correspondingly, the concentration of oxygen is shown as partial pressure. The concentration of oxygen decreases from a concentration $P_o(1)$ in the gas casing 11 at an upper face 20 of the second plug 13 through the second plug 13 and through the reaction space 15 to a certain percentage, but not zero percent, in the reaction zone 18. From the reaction zone 18 and further through the reaction space 15 the concentration of oxygen decreases with a less steep gradient than the gradient from the gas casing to the reaction zone.

FIG. 3F and FIG. 3G shows that the transducer signal, illustrated by the arrows, is independent of the plane in which the reaction zone 18 is located. The transducer signal is only dependent on the concentration $C_{O_2}$ of oxygen and the concentration $C_{CH_4}$ of methane and of the diffusional characteristics of the sensor components, which are fixed physical values.

In the following, the principle for measurements with the microsensor according to the invention will be described in further detail referring to the mathematical basis for the measurements with the microsensor according to the invention.

The methane microsensor principle is based on a counter-diffusion principle where methane oxidising bacteria in the reaction space consume oxygen from the gas capillary when the sensor tip is exposed to methane. This oxygen consumption results in a lowering of the oxygen tension inside the reaction space, which is sensed by the internal oxygen microsensor. In contrast to the new calibration method, this procedure leads to some scatter due to inaccuracies during gas sampling and storing for subsequent analysis. The response is linear and very stable over time and this fact gives a hint on the detailed functioning of the sensor. If the response was closely related to the physiological state and motility of the methane oxidizing bacteria it might be expected to change over time as a function of time dependent changes in the bacterial population. But once the signal reaches stability after some days of enrichment the signal often stays practically on the same level for the rest of its lifetime, which so far has been more than 3 months. This can be explained by FIG. 3E–3G: as the sensor is exposed to a methane partial pressure, $P_m^e$ during enrichment the microorganisms multiply, making the methane oxidizing activity more intense, locally depleting the oxygen or methane until methane oxidation only can occur in a zone at a distance a from the gas phase in the gas capillary, a zone whereto both substances are supplied by diffusion. The sizes of these diffusional fluxes must match the stochiometry of the methane oxidation reaction:

$$CH_4 + 2O_2 \rightarrow CO_2 + 2H_2O,$$

for simplicity ignoring the fraction of carbon from methane that is incorporated into biomass. If the bacteria can concentrate their activity into a very narrow zone, the relationship between the steady-state diffusional fluxes of oxygen and methane in the reaction space, $J_o$, and $J_m$, can be described by Fick's 1. law, assuming a one-dimensional diffusion model of the sensor and for simplicity assuming identical diffusional properties in water and silicone rubber:

$$J_o = 2 \cdot J_m$$

$$-D_o \cdot \frac{-C_o(1)}{\underset{a}{(1)}} = 2 \cdot -D_m \cdot \frac{-C_m(3)}{1-a}$$

where $C_o(1)$ and $C_m(3)$ are the concentrations of oxygen at position 1 and methane in position 3, respectively, and I is the combined length of the diffusion paths, i.e. the length of the reaction space plus the lengths of the two silicone membranes. $D_o$ and $D_m$ are the diffusion coefficients in the sensor of oxygen and methane, respectively.

Using the relationship between concentration (C), solubility ($\alpha$), and partial pressure (P), $C = \alpha \cdot P$, and substituting this into equation 1 yields:

$$\frac{D_o \alpha_o \cdot P_o(1)}{a} = 2 \cdot \frac{D_m \alpha_m \cdot P_m^e(3)}{1-a} \quad (2)$$

From simple geometric considerations, the, following relationship is obvious:

$$\frac{P_m^e(3)}{a-p} = \frac{P_o(1)}{a} \quad (3)$$

where p is the distance between the gas space and position s and $P_o^e(s)$ is the partial pressure of oxygen at position s.

Position s is the position of the tip of the internal oxygen sensor (see FIG. 1). Solving equation (2) for a and substituting into equation (3) yields the following expression for the partial pressure at the tip of the internal oxygen sensor at the end of enrichment:

$$P_o^e(s) = -2 \cdot \frac{D_m \alpha_m}{D_o \alpha_o} \cdot \frac{p}{l} \cdot P_m^e(3) + P_o(1) \cdot \left(1 - \frac{p}{l}\right) \quad (4)$$

If the sensor after enrichment is exposed to a lower partial pressure of methane, $P_m(3)$, during calibration and measurements, the bacteria might be able to move to a new location where both oxygen diffusing front the gas capillary and methane diffusing from the sensor tip are completely consumed, or the bacteria are not immediately motile and will consume all methane diffusing in from the tip in the same zone as where the enrichment took place, whereby not all of the oxygen diffusing front the gas capillary can be consumed.

If the cells are perfectly motile and consume all of both oxygen and methane in a new position, the situation is equivalent to the enrichment situation yielding the following expression for the oxygen partial pressure at the tip of the internal oxygen sensor with completely motile methane oxidation capacity:

$$P_o(s) = -2 \cdot \frac{D_m \alpha_m}{D_o \alpha_o} \cdot \frac{p}{l} \cdot P_m(3) + P_o(1) \cdot \left(1 - \frac{p}{l}\right) \quad (5)$$

If the cells are fixed in the enrichment zone, the following expression describes the steady-state fluxes of oxygen and methane.

$$J_o^{1,2} - J_o^{2,3} = 2 \cdot J_m \quad (6)$$

where $J_o^{1,2}$ and $J_o^{2,3}$ are the fluxes of oxygen in the zones between the gas phase and the enrichment zone, and between the enrichment zone and the sensor tip, respectively. Using Fick's 1. law of diffusion and substituting solubilities times partial pressures for concentrations yields:

$$D_o \alpha_o \frac{P_o(2) - P_o(1)}{a} - D_o \alpha_o \frac{-P_o(2)}{1-a} = 2 \cdot D_m \alpha_m \frac{-P_m(3)}{1-a} \quad (7)$$

From geometrical reasons the following relation exists between the partial pressures of oxygen at positions 1, 2 and s:

$$\frac{P_o(s) - P_o(1)}{a - p} = \frac{P_o(1) - P_o(2)}{a} \quad (8)$$

Solving equation (7) for $P_o(2)$ and substituting into equation (8) yields the following expression for a fixed methane oxidation capacity:

$$P_o(s) = -2 \cdot \frac{D_m \alpha_m}{D_o \alpha_o} \cdot \frac{p}{l} \cdot P_m(3) + P_o(1) \cdot \left(1 - \frac{p}{l}\right) \quad (9)$$

Comparing equations (5) and (9) shows that $P_o(s)$ is the same whether or not the methane oxidation capacity is fixed at the enrichment zone. This may be the explanation for the reproducibility of the calibration curves even when the sensor is used under varying concentration ranges that might give rise to changes in the position of the active bacterial population. Furthermore, the model predicts the signal to be a linear function of the methane at the sensor tip, $P_m(3)$ as the signal of the internal oxygensensor is proportional to $P_o(s)$.

The model presented above describes situations with no oxygen in the external medium ($P_o(3)=0$) and it assumes that diffusivities of oxygen and methane are identical in silicone rubber and in aqueous media and that the oxidation zone is infinitely narrow. Furthermore, the oxygen consumption of the internal oxygen microsensor is assumed to be negligible. Neither of these assumptions are realistic, but a similar but more complex mathematical model for a broader oxidation zone still predicts linearity, and independence of both the width and the position of the methane oxidation zone is predicted for diffusivities that vary in silicone and aqueous media if the ratio of the diffusion coefficients of oxygen and methane is constant throughout the sensor. The actual width of the oxidation zone is not resolved here, but as some sensors have a linear response up to a methane partial pressure of 1 atmosphere with a reaction space length of 150 microns, the width of the methane oxidation zone when the sensor is exposed to a methane partial pressure of a fraction of an atmosphere must be only a corresponding fraction of the reaction space length or less, assuming a constant specific reaction rate.

Due to the miniaturisation of the sensor, it is almost insensitive to stirring in the surrounding environment, and is thus well suited for in-situ measurements.

Figure 4:
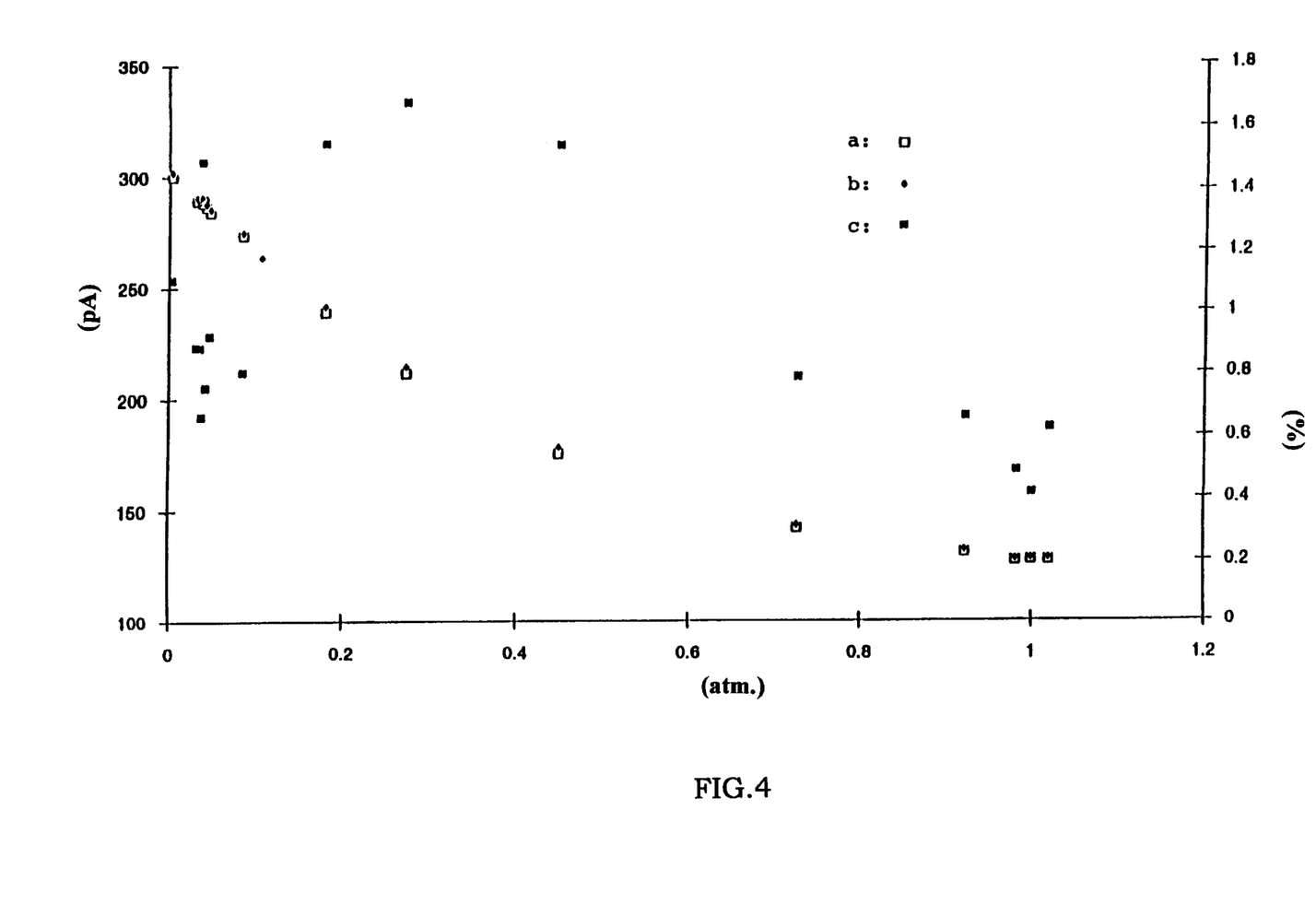
FIG. 4 is a curve illustrating the signal of a transducer as a function of the concentration of a primary substrate in the form of methane under stirring and not stirring, respectively, while measuring in fluid.

FIG. 4 is a graphical illustration of a series of experiments investigating the sensitivity of the sensor to stirring in the surrounding environment in which the measurement are performed. In the experiments the measurements are made in a fluid containing methane. The partial pressures of methane in the fluid are shown on the abscissa, the left ordinate shows the measured signal, and the right ordinate shows the stirring effect as a percentage of the maximal change in signal from 0 to 100% methane. The series of points marked 'a' show the signal in non-stirred fluid, the series of points marked 'b' show the signal in stirred fluid, and points marked 'c' show the effect of stirring.

The graph shows an increase in the effect of stirring in the range 0–0.3 atm. partial pressure of methane, while the effect of stirring decreases at higher partial pressures. In general, the effect of stirring is below 2% for the experiments.

Figure 5:
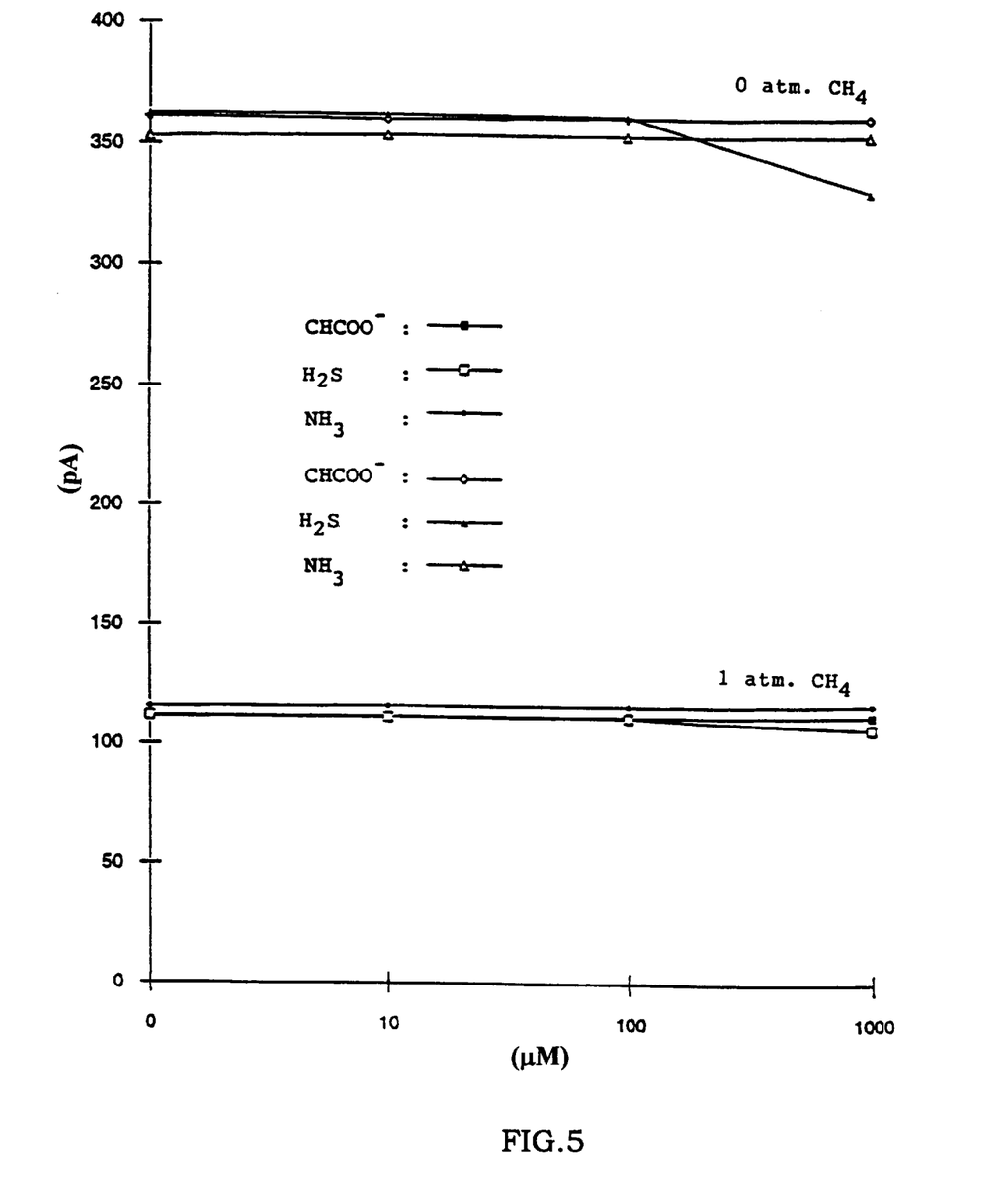
FIG. 5 is a curve illustrating the degree of interference from acetate, sulphide, and ammonia when measuring in fluid containing 0 and 1 atm. partial pressure of methane, respectively.

FIG. 5 graphically illustrates the result of a series of experiments investigating the sensor sensitivity to interference from other substances than methane, namely acetate ($CH_3COO-$), sulphide ($H_2S$), and ammonia ($NH_3$). These substances were chosen because they occur in sediments and bio-gas reactors, which are some of the main areas for use of the sensor according to the invention. The concentration of acetate, sulphide, and ammonia is shown on the abscissa, and the sensor signal is shown on the ordinate. The graph comprises a first upper set of curves corresponding to concentrations of acetate, sulphide, ammonia at a methane partial pressure of 0 and a lower set of curves corresponding to concentrations of acetate, sulphide, and ammonia at a methane partial pressure of 1 atm. The experiments with acetate and sulphide are performed in phosphate ($PO_4^{3-}$) buffer pH 7, while the experiments with ammonia is performed in a glycine ($NH_2CH_2COOH$) buffer pH 10.

The graph shows that the sensor sensitivity to interference from the three compounds is practically zero except for some sensitivity to sulphide at high concentrations. This interference can be compensated for using the aforementioned front guard.

The invention is described in FIG. 1 and FIG. 3A–3G referring to a specific embodiment of a microsensor. However, the design of the sensor can be different. Furthermore, the experiments illustrated in the graphs should not be considered a exhaustive description of the properties of the microsensor.

The present invention also relates to a microsensor for measuring a substrate in an surrounding environment such as a fluid, a gas or a matrix. The microsensor comprises a reaction space containing biologically active or catalytic material for consumption or conversion of the substrate with the concomitant consumption of a cofactor, a diffusion permeable outer barrier delimiting the reaction space, and a detector of the cofactor positioned at a certain distance from the outer barrier;

A sensor of this type is known from Electroanalysis, 1 (1989) 305–309. The reaction space in the sensor described there contains an alginate matrix containing bacteria, which assimilate $CO_2$ thereby using oxygen as a cofactor. The reaction space is surrounded by a diffusion permeable membrane enclosing the space. The membrane enables diffusive transport of $CO_2$ and oxygen into the reaction space. Below the reaction space a Clark-type polarographic oxygen detector is constructed. The entire structure is made on a silica wafer using photo-lithographic processes.

The concentration of $CO_2$ in the surrounding environment determines the diffusive flux of $CO_2$ into the reaction space, which in turn determines the oxygen consumption. The oxygen consumption in the reaction space reduces the flux of oxygen, which likewise diffuses from the surrounding environment through the reaction space down to the oxygen detector. The signal from the oxygen detector thus decreases with an increase in the $CO_2$ concentration in the surrounding environment.

The known sensor has the disadvantage, however, that both the substrate to be measured ($CO_2$) and the cofactor ($O_2$) have to be present in the surrounding environment to make a measurement possible. Furthermore, a variation in concentration of the cofactor in the surrounding environment will cause variations in the signal even if the concentration of the substrate to be measured is unchanged.

According to the invention as stated in claim 11, these disadvantages are eliminated by the facts that the reaction space is enclosed in a casing of a non-permeable material with an opening in which the outer barrier is placed, that the microsensor comprises a non-permeable second casing adjacent to the reaction space, that the cofactor is present in a reservoir in the second casing, that the second casing has a connecting opening between the reservoir and the reaction space, that the connecting opening is located at a distance from the outer opening, that a diffusion permeable middle barrier is placed in the connecting opening, and that the detector is placed in the reaction space or in the middle barrier.

The presence of the cofactor in an internal reservoir in the sensor makes it more universally applicable as it can measure the substrate in question even in environments where the cofactor is not present. Furthermore, the sensitivity to variations in the cofactor concentration in the surrounding environment is decreased, as the internal cofactor up to a certain limit will supply the main contribution to the reaction in the reaction space. Thus the sensor is well suited for in-situ measurements in process reactors, for instance sewage treatment plants, where there is some variation in the composition of the surrounding environment. A sensor with these characteristics is very accurate and it can be made with such small dimensions that it can be used for measurements of gradients in the environments to be analysed. A very high spatial resolution in even very steep chemical gradients can be achieved.

By furnishing the sensor with a encompassing guard casing, as stated in claim 12, and a trap for the cofactor, which allows the substrate to be measured to pass, the sensitivity to the presence of the cofactor in the surrounding environment can be further decreased. This introduces the minor disadvantage that the increased distance of diffusion for the substrate to be analysed causes the response time of the sensor to increase to a certain extent, which, however, is not of great importance in practice. The trap or guard measures for the cofactor can with advantage be chosen as stated in claim 13 or 14.

A further stabilisation of the working properties sensor of the sensor can be achieved, if the sensor, as stated in claim 15, is furnished with a reservoir or diversion space which can assimilate surplus cofactor or products of the reaction or conversion from the process taking place in the reaction space. The opening to the diversion space will to a large extent function as a concentration fix point for the diffusion processes taking place in the sensor. Preferable embodiments are stated in claims 16 to 18.

Two preferred embodiments of the sensor are stated in claim 19 and 20. During experiments with a methane sensitive sensor as stated in claim 20, where the cofactor is oxygen, interference from other compounds such as acetate, sulphide, and ammonia was investigated. The experiments showed that interference from these compounds is negligible, only very high concentrations of sulphide had some effect.

Interference from different pH values in the fluid wherein the measurements were made was practically zero and deviated only as a consequence of using different buffers and of the different physical properties of these buffers. Results showed an interference of less than 4% between measurements at pH 7 and pH 10, respectively.

The temperature of the environment in which measurements are made will influence the measurements to some extent. Furthermore, the sensor cannot be used above the temperatures at which the chemical or biological components used in the reaction space will be inactivated.

If the cofactor is oxygen, the detector is preferably electrochemical (claim 21), for instance the Clark-type oxygen microsensor, but other types such as optical detectors (claim 22) may also be applied. Fibre-optical oxygen microsensors are known from the literature.

The various diffusion permeable barriers delimiting the compartments of the microsensor have the function, among other things, to protect the materials in these spaces against desiccation and to prevent their dispersion. The barriers are preferably silicabased materials, which have proven to have a suitable permeability to especially gasses. However, materials, which are permeable to diffusion of ions or polar compounds, can be used in combination with the use of micro-organisms capable of metabolising these ionic/polar compounds in the reaction space.

Measurements with the sensor can be performed in-situ and can be made within a response time of down to ½ minute. Thus the presence of for instance methane in for instance a fluid can be measured within a very short time and be measured continuously over a given period of time. The response time is mainly dependent on the dimensions of the sensor.

Experiments have shown that the sensor can be minimised to such an extent that the sensitivity to stirring is below 2%. Thus the sensor according to the invention has no need for stirring. Furthermore, it is possible to produce a methane sensor with a signal, which is linear in the range of methane partial pressure from 0 to 1 atm. and with a sensitivity down to 0.001 atm. of methane.

The sensor according to the invention is primarily intended for the measurement of ethanol, methanol, ammonium and methane in microbial ecology, medicine, and in the control of industrial processes, including waste water treatment plants. Industries, producing measuring equipment, and industries, producing organic compounds in fermentors, are suited areas for the use of the sensor according to the invention. Furthermore, the sensor is well suited for use in bio-gas reactors and laboratories. It can be manufactured in glass using techniques for blowing and pulling glass described in the literature, using photolithographic processes, or using other suited processes, for instance those used in the fabrication of micro-mechanical components.

We claim:

1. A microsensor for measuring the concentration of a substance in an environment such as a liquid, a gas or a matrix, which microsensor comprises:

a reaction space containing biologically active or catalytic material for consuming or transforming the substance during concurrent consumption or concurrent transformation of a co-factor, a diffusion permeable outer barrier for delimitation of the reaction space, and a detector for the co-factor placed at a distance from the outer barrier;

the reaction space comprising a diffusionally tight first casing with an entrance opening, in which the outer barrier is placed, the microsensor further comprising a diffusion impermeable second casing, which abuts the reaction space, the co-factor being present in a supply space in the second casing, the second casing having a connection opening between the supply space and the reaction space, the connection opening being arranged at a distance from the entrance opening, a diffusion permeable middle barrier being located in the connection opening, and the detector being located in the reaction space or in the middle barrier.

2. A microsensor according to claim 1, in which the first casing is surrounded by a diffusion impermeable shielding casing with a shielding opening, in which a diffusion permeable shielding barrier is placed, and in the shielding casing between the shielding barrier and the outer barrier of the first casing a shielding space is made with shielding means to consume the co-factor without consuming the substance.

3. A microsensor according to claim 2 in which the shielding means comprise a material comprising microorganisms.

4. A microsensor according to claim 3, in which the shielding means comprise an electrolyte, which is in connection with an electrode.

5. A microsensor according to claim 1, in which in the first casing a deflection space is made for assimilation of the co-factor or possible products from the transformation of the substance with the co-factor, and a deflection opening is present between the reaction space and the deflection space, the deflection opening being arranged at a distance from the entrance opening.

6. A microsensor according to claim 5, in which a diffusion permeable deflection barrier is present in the deflection opening.

7. A microsensor according to claim 5, in which deflection means are present in the deflection space for consuming the co-factor.

8. A microsensor according to claim 7, in which the deflection means comprises an electrolyte, which is in connection with an electrode.

9. A microsensor for measuring the concentration of a primary substrate in an environment, such as a fluid, a gas or a matrix, which microsensor comprises a first casing with an opening which is in contact with a first barrier and a reaction space which borders on the first barrier, in which reaction space a catalytic material is located, a material intended to catalyse a conversion of the primary substrate with the concomitant conversion of a secondary substrate, the microsensor further comprises a transducer for the secondary substrate, the transducer being located at a predetermined distance from the first barrier, the microsensor having a second casing, the second casing having an opening in contact with a second diffusion permeable barrier, the second barrier being established at a distance from the first barrier so that the reaction space is formed in the first casing between the first barrier and the second barrier, and the second casing constituting a source of the secondary substrate.

10. A microsensor according to claim 9, in which a third casing extends around the first casing and is provided with an opening, which abuts a third barrier arranged at a distance from the first barrier.

11. A microsensor according to claim 9, in which the reaction space contains an environment with chemical or biological components, the second casing contains a secondary substrate, and the transducer includes means for determining, by measuring the secondary substrate, the concentration of the primary substrate.

12. A microsensor according to of claim 10, in which the third casing is provided with an oxygen consuming device, and the oxygen consuming device is selected from the group comprising electro-chemical cathodes and bacteriological cell structures.

13. A microsensor according to claim 9, in which the first casing is provided with an oxygen consuming device, and the oxygen consuming device is selected from the group comprising electro-chemical cathodes and physical means.

14. A microsensor according to claim 9, in which the reaction space contains methane oxidising bacteria, the supply space contains atmospheric air, and the detector includes means to detect oxygen.

15. A microsensor according to claim 9, in which the reaction space contains an environment with methane oxidising bacteria, the second casing contains atmospheric air, and the transducer includes means for determining, by measuring the concentration of oxygen at a predetermined distance from the first barrier, the presence of methane in the medium.

16. A microsensor according to claim 1, in which the reaction space contains ammonia oxidising bacteria, the second casing contains atmospheric air, and the detector includes means to detect oxygen.

17. A microsensor according to claim 9, in which the reaction space contains an environment with ammonia oxidising bacteria, the second casing contains atmospheric air, and the transducer includes means for determining, by measuring the concentration of oxygen in a predetermined distance from the first barrier, the presence of ammonia in the medium.

18. A microsensor according to claim 1, in which the detector is an electro-chemical detector.

19. A microsensor according to claim 1, in which the detector is an optical detector.

20. A microsensor according to claim 1, in which at least some of the barriers are made of a material based on silicone.

21. A microsensor according to claim 20, in which the first barrier and the second barrier are made of silicone.

22. A microsensor according to claim 20, in which the first, the second and the third barrier are made of silicone.

23. A microsensor according to claim 1, in which at least some of the casings are made of glass.

24. A microsensor according to claim 23, in which the first casing and the second casing are made of glass.

25. A microsensor according to claim 23 in which the first, the second and the third casing are made of glass.

26. The use of a microsensor according to claim 1 for measuring the presence of a primary substrate in an environment in the shape of a liquid, a matrix or a gas.

27. The use of a microsensor according to claim 9 for measuring the presence of a primary substrate in an environment in the shape of a liquid, a matrix or a gas.

* * * * *